United States Patent
Fukaya et al.

[11] Patent Number: 5,859,361
[45] Date of Patent: Jan. 12, 1999

[54] AIR FUEL RATIO SENSOR AND A METHOD FOR MAKING THE SAME

[75] Inventors: Kenji Fukaya, Oobu; Masato Yamamoto, Ama-gun; Makoto Hori, Oogaki; Masahiro Hamaya, Anjo; Minoru Ohta, Okazaki, all of Japan

[73] Assignee: Denso Corporation, Kariya, Japan

[21] Appl. No.: 908,799

[22] Filed: Aug. 8, 1997

[30] Foreign Application Priority Data

Aug. 9, 1996 [JP] Japan ..................................... 8-210941

[51] Int. Cl.⁶ ........................... G01N 27/46; G01N 27/22; H01C 13/00; F02M 7/00
[52] U.S. Cl. ........................... 73/23.2; 73/23.32; 338/34; 204/431; 427/372.2; 422/94
[58] Field of Search .................................. 73/23.2, 23.32, 73/23.31; 338/34; 427/372.2; 422/94; 204/431

[56] References Cited

U.S. PATENT DOCUMENTS

| | | | |
|---|---|---|---|
| Re. 33,980 | 6/1992 | Matsuura et al. | 422/98 |
| 3,844,920 | 10/1974 | Burgett et al. | 204/195 S |
| 3,936,794 | 2/1976 | Beaudoin et al. | 338/34 |
| 3,959,765 | 5/1976 | Stewart | 338/34 |
| 4,383,906 | 5/1983 | Sano et al. | 204/416 |
| 4,526,672 | 7/1985 | Reed | 204/428 |
| 4,535,316 | 8/1985 | Wertheimer et al. | 338/34 |
| 4,611,562 | 9/1986 | Nakano et al. | 123/440 |
| 5,228,975 | 7/1993 | Yamada et al. | 204/424 |
| 5,593,558 | 1/1997 | Sugino et al. | 204/429 |
| 5,627,306 | 5/1997 | Yamauchi et al. | 73/23.2 |

FOREIGN PATENT DOCUMENTS

| | | |
|---|---|---|
| 2-216448 | 8/1990 | Japan . |
| 57-82762 | 5/1992 | Japan . |
| 7-83045 | 3/1995 | Japan . |
| 8-052530 | 2/1996 | Japan . |

*Primary Examiner*—Hezron E. Williams
*Assistant Examiner*—J. David Wiggins
*Attorney, Agent, or Firm*—Pillsbury Madison & Sutro LLP

[57] ABSTRACT

An air fuel ratio sensor has a sensor element having a sensing portion and a flange portion in contact with a tapered portion of an accommodation hole of a housing. The sensor element is hot crimped at a hot crimping portion of a housing. At least the hot crimping portion is made of a ferritic stainless steel formed by cold forging and having a composition content comprising a total amount of C and N impurities of 0.03 wt % or below. The average hot crimping temperature of the housing is performed at lower than 1000° C. as applied for a time period of one second or less.

7 Claims, 5 Drawing Sheets

AIR FUEL RATIO SENSOR AND A METHOD FOR MAKING THE SAME

BACKGROUND OF THE INVENTION

1. Field of the Invention

This invention relates to a sensor, and more particularly, to an improved air fuel ratio sensor which has a housing formed by cold forging and a detector element fixed in the housing by crimping or staking under hot conditions. The invention also relates to a method for making such a sensor as mentioned above.

2. Description of the Prior Art

As is well known in the art, air fuel ratio sensors are arranged to detect an air fuel ratio in a gas to be measured using a signal from a pair of electrodes provided at one end of a sensor element. The sensor element is fixedly held in a accommodation hole of a housing. Where such an air fuel ratio sensor is adopted, for example, in automotive vehicles, they are inevitably exposed to water, soil, or de-frosting fluids. Accordingly, care should be taken to corrosion resistances of members which are used to constitute an air fuel ratio sensor.

To this end, it is usual to use a ferritic stainless steel of a high corrosion resistance as a housing for airtightly fixing the sensor element therewith. The housing hitherto employed for this purpose is made of ferrite-base stainless steels of good machinability. Such steels are so hard that the housing is formed by machining.

The housing essentially requires an accommodation hole wherein a sensor element is accommodated. For the formation of the hole, a material for the housing has to be machined in large quantities, e.g. about 70% of the starting steel for the housing is usually wasted in vain by machining.

To avoid the wastage of the steel, attempts have been made wherein the housing is not formed by machining, but through cold forging.

However, where a housing is formed by forging, ferritic stainless steels of the type as used for the machining cannot be employed because of the difficulty in cold forging of the stainless steels. In short, different types of ferritic stainless steels, which have properties suitable for the cold forging, become necessary.

In the fabrication of conventional air fuel ratio sensors, it is usual to form a housing having an accommodation hole, place a sensor element in the accommodation hole, and subject the accommodated element to crimping under hot or heating conditions to fixedly hold the sensor element in the hole of the housing.

However, the housing obtained by cold forging has the problem that seawater or rainwater is prone to infiltrate from the thermally crimped portion thereof, thereby causing the housing to be corroded.

SUMMARY OF THE INVENTION

It is accordingly an object of the invention to provide an air fuel ratio sensor which can overcome the problems involved in prior art counterparts.

It is another object of the invention to provide an air fuel ratio sensor which has a housing obtained by cold forging and a sensor element fixed to the housing by crimping or staking under heating conditions and has a good corrosion resistance.

It is a further object of the invention to provide a method for making such a sensor as mentioned above.

According to one embodiment of the invention, there is provided an air fuel ratio sensor which comprises:

a sensor element having, at one side thereof, an elongated sensing portion closed at an end thereof and capable of detecting an air fuel ratio in a gas to be measured, a flange portion formed at the intermediate of said element, and a hollow portion extending from the flange portion at the other end of said element and having an open end; and a housing having an accommodation hole extending along an axial direction thereof and capable of accommodating the sensor element therein so that the sensing portion extends through the accommodation hole from one side of the housing, wherein the accommodation hole has a tapered inner wall serving as a stopper of the flange portion of said sensor element and the housing has a hot crimped portion at the other side thereof to fixedly hold the hollow portion of the sensor element within the accommodation hole, at least the hot crimped portion of the housing being made of a ferritic stainless steel with its composition comprising a total content of carbon and nitrogen of 0.03 wt % or below.

Preferably, the housing is entirely made of the ferritic stainless steel comprising a total content of carbon and nitrogen of 0.03 wt % or below.

According to another embodiment of the invention, there is also provided a method for making an air fuel ratio sensor of the type which comprises a sensor element having, at one side thereof, an elongated sensing portion closed at an end thereof and capable of detecting an air fuel ratio in a gas to be measured, a flange, portion formed at the intermediate of said element, and a hollow portion extending from the flange portion at the other end of said element and having an open end, and a housing having an accommodation hole extending along an axial direction thereof and capable of accommodating the sensor element therein so that the sensing portion extends through the accommodation hole from one side of the housing, wherein the accommodation hole has a tapered inner wall serving as a stopper of the flange portion of the sensor element and the housing has a hot crimped portion at the other side thereof to fixedly hold the hollow portion of the sensor element within the accommodation hole, the method comprising forming said housing by cold forging, and hot crimping of the housing is performed under conditions of an average temperature lower than 1000° C. and a time of one second or below.

PREFERRED EMBODIMENTS OF THE INVENTION

We have made studies on the problem that housings obtained by cold forging are susceptible to corrosion.

Figure 6:
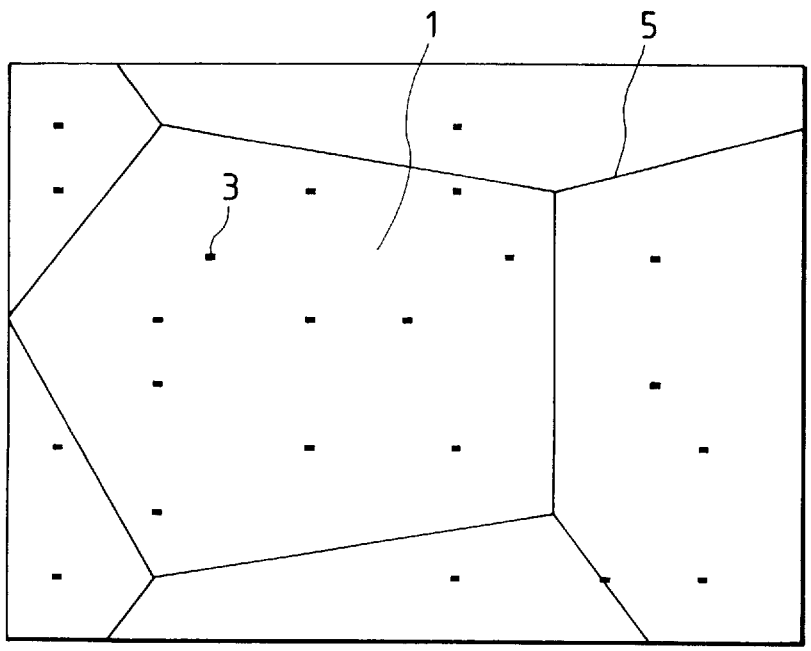
FIG. 6 is a schematic illustrative view showing the crystal state of a stainless steel for machining when the steel is crimped under heating conditions.
Figure 7:
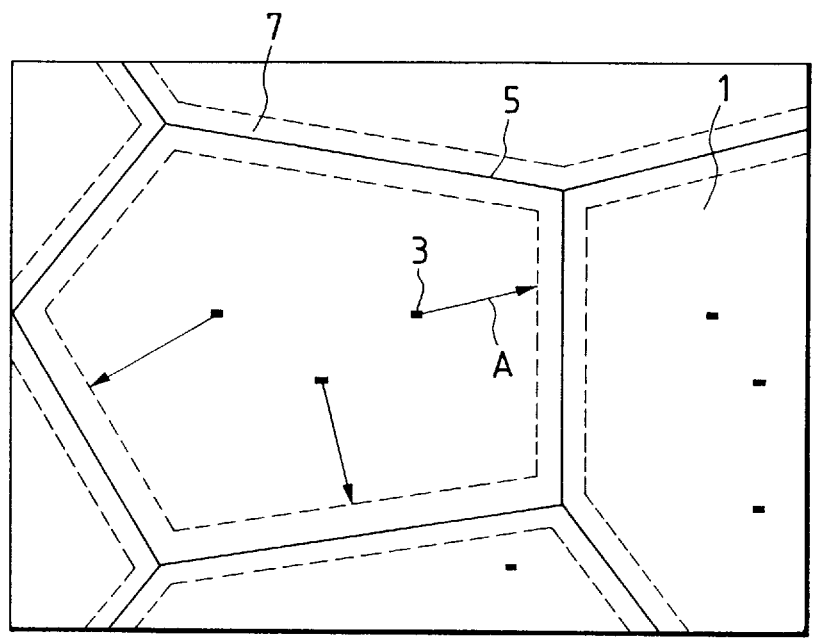
FIG. 7 is a schematic illustrative view showing the crystal state of a stainless steel for cold forging when the steel is caulked or crimped under heating conditions.

Reference is now made to FIGS. 6 and 7 which, respectively, illustrate the crystal state of a hot crimped portion of a ferritic stainless steel for machining and a ferritic stainless steel for cold forging. It will be noted that the term "hot crimping" used herein means crimping by application of heat.

In FIG. 6, reference numeral 1 indicates a crystal of Fe—Cr which is a main component of the ferritic stainless steel and reference numeral 5 indicates an impurity present in the Fe—Cr crystals 1. The impurity consists of carbon and/or nitrogen. As shown in FIG. 6, after the ferritic stainless steel for machining has been hot crimped, grain boundaries 5 between the Fe—Cr crystals 1 are tightly combined together, thereby preventing water and the like from infiltration from outside. The housing made of the machining ferritic stainless steel is resistant to corrosion.

On the other hand, the crystal state of a ferritic stainless steel for cold forging which has been subjected to hot crimping is illustrated with reference to FIG. 7.

In FIG. 7, reference numeral 1 indicates crystals of Fe—Cr which is a main component of a ferritic stainless steel for cold forging, and reference numeral 3 indicates an impurity present in the Fe—Cr crystals 1 as in FIG. 6. The impurity consists of carbon and/or nitrogen.

As shown in FIG. 7, the ferritic stainless steel for cold forging suffers an influence of heat at the time of the hot crimping. As shown by the arrows A in FIG. 7, the impurity 3 such as C or N in the Fe—Cr crystals segregates toward a grain boundary 5 between the Fe—Cr crystals. The thus segregated impurity combines with Cr existing at the interface of the grain boundary, thereby forming a compound such, as Cr—N, Cr—C of the like.

Accordingly, the ratio of Cr is reduced at the interface of the grain boundary between adjacent Fe—Cr crystals on comparison with a ratio of Cr in the Fe—Cr crystals. This results in the formation of a Cr deficient layer 7.

More particularly, ferritic stainless steels for colds forging suffer the influence of high temperatures at the time of hot caulking or crimping, so that the Cr deficient layer 7 is formed. Water is very liable to infiltrate from the deficient layer of Cr, thereby presenting the problem of corrosion.

The reason why no deficient layer 7 is formed in the case of a ferritic stainless steel for machining but such a layer 7 is formed for a ferritic stainless steel for cold forging has been checked. As a result, it has been found that ferritic stainless steels for machining contain sulfur (S) as an impurity, which is not usually contained in a ferritic stainless steel for cold forging. This sulfur acts to suppress the movement of other impurities including C and N as will be caused by application of heat.

In order not to form any Cr deficient layer in the crystal grain boundary, it will be sufficient to cause an impurity such as C or N not to segregate at the interface of the Fe—Cr crystals when a ferritic stainless steel for cold forging is exposed to high temperatures at the time of crimping.

More particularly, a housing for an air fuel ratio sensor is so arranged that at least a portion thereof, which is exposed to the highest temperature during the course of hot crimping, is made of a ferric stainless steel composition which has the following content of carbon and nitrogen impurities carbon (C)+nitrogen (N)≦0.03 wt %

When the impurities in the Fe—Cr crystals of a ferric stainless steel for cold forging are preliminarily reduced in content as defined above, the amount of the impurities to segregate toward the interface 5 of the crystals can be reduced. As a result, the deficient layer 7 is very unlikely to be formed.

According to the method of the invention, when the hot crimping is carried out at a maximum temperature lower than 1000° C. for a time of 1 second or below, the movement of the impurity 3 toward the interface 5 of the crystals can be appropriately suppressed. Thus, the amount of the impurity being segregated toward the interface 5 can be reduced, thereby suppressing the formation of the deficient layer 7.

The portion of the housing, which becomes the highest in temperature when hot crimped, should preferably have a deviation of a distance between the outer peripheral surface of the portion and the inner peripheral surface of the accommodation hole which is less than 15% relative to an average thickness of the housing. This is because when the thickness of the housing is non-uniform, heat is concentrated on a thinner portion even if hot crimping temperature is low. Such a thin portion is undesirably heated to a temperature higher than as required.

When the thickness of the portion to be hot crimped is defined as set out above, uniform heat generation at the time of the hot crimping is ensured throughout the portion, resulting in the satisfactory suppression of the deficient layer from being formed. The maximum hot crimping temperature should more preferably be 950° C. or below.

The air fuel ratio sensor according to the invention is more particularly described with reference to FIG. 1.

Figure 1:
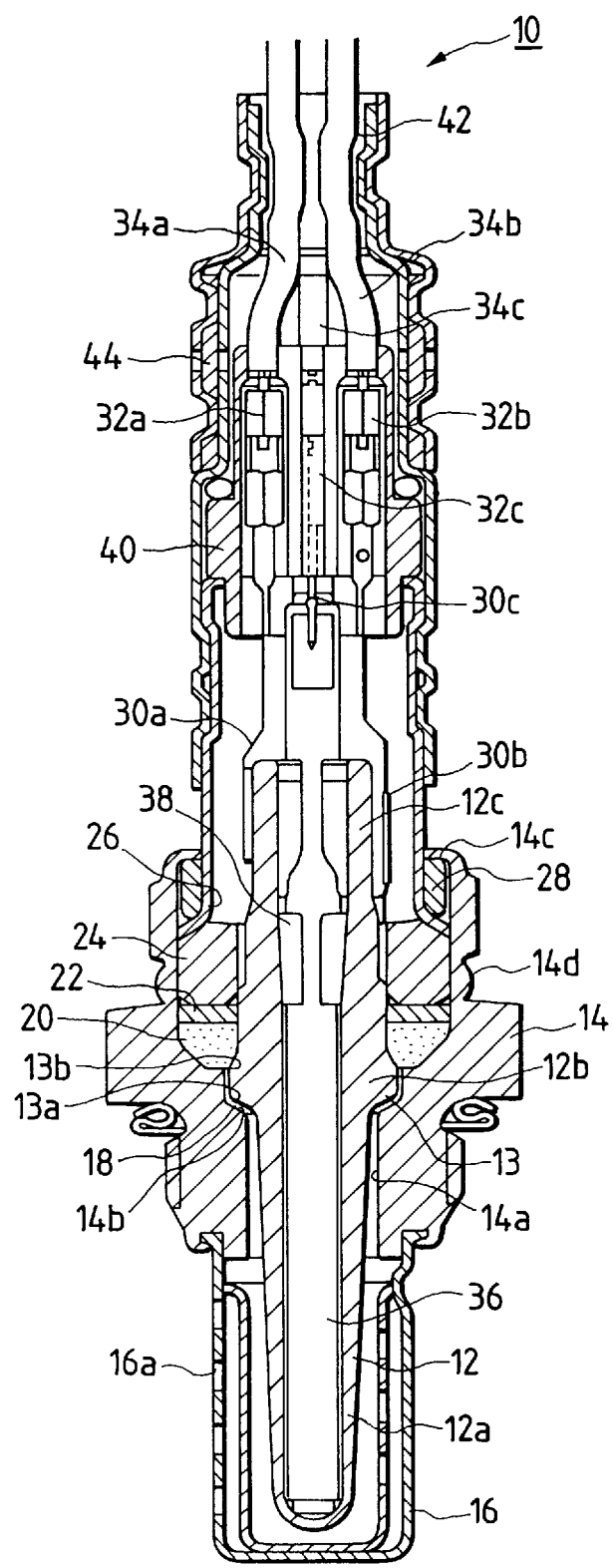
FIG. 1 is a sectional view of an air fuel ratio sensor according to the invention.

In FIG. 1, there is generally shown an air fuel ratio sensor 10. The sensor includes a sensor element 12 in the form of a cup closed at an one end thereof. The cup-shaped sensor element 12 has an elongated sensing unit 12a at one side thereof wherein an air fuel ratio of a gas to be measured is detected, a flange portion 12b serving as a stopper when inserted into a housing 14 and formed at the intermediate of the cup-shaped element 12, and a hollow portion 12c extending from the flange portion at the other side of the element 12 and having an open end.

The sensor element 12 is made, for example, of zirconia. Although not particularly shown in FIG. 1, the sensor element 12 is provided with a measuring electrode and a reference electrode on outer and inner surfaces thereof. A signal outputted from the electrodes is used to measure an air fuel ratio of a gas to be measured. This type of sensor is well known in the art and is not further described herein.

The sensor element 12 is accommodated in an accommodation hole 14a formed in the housing 14 such that part of the sensing unit 12a extends outwardly from one end of the housing as shown.

The housing 14 at least at a portion to be crimped as will be described hereinafter is mainly composed of a ferritic stainless steel which comprises a total amount of C and N impurities of not greater than 0.03 wt %. The ferritic stainless steel useful in the practice of the invention should preferably be for cold forging and comprises 16.0 to 18.0 wt % of Cr, 0.75 wt % or below of Si, 1.00 wt % or below of Mn, 0.040 wt % of below of P, 0.030 wt % or below of S, and the balance being Fe and inevitable impurities provided that the total amount of C and N is 0.03 wt % or below.

The sensing unit 12a extending from the housing 14 is covered with a protective cover 16 as shown. The protective cover 16 has a plurality of through-holes 16a. A gas to be measured is passed through the through-holes 16a and arrives at the sensing unit 12a of the sensor element 12.

The protective cover 16 is provided in order to protect the sensor element 12 from impurities in an exhaust gas to be measured.

The accommodation hole 14a is tapered as 14b, which is in contact with a lower end face 13a of the flange portion 13 of the sensor unit 12 via a metal washer 18 when the sensor unit 12 is inserted into the hole 14a.

At an upper face 13b of the flange portion 13 of the sensor element 12, there are provided, in this order, an insulating powder 20 such as talc, an insulating ring 22 made, for example, of vermiculite, an insulating member 24 made, for example, of an electrical porcelain, a cover 26, and a ring 28 made of a metal as shown. The sensor element 12 is fixedly held within the accommodation hole 14a of the housing 14 by crimping at a cold crimped portion 14c and a hot crimped portion 14d of the housing 14.

Upon the hot crimping, the insulating powder 20 and the like insulating members are so deformed that the airtightness of the housing at opposite sides is ensured.

The electrodes (not shown) of the sensing unit 12a of the sensor element 12 are, respectively, lead to the other side of the housing and are, respectively, electrically connected to intermediate leads 30a, 30b. The intermediate leads 30a, 30b are, in turn, electrically connected via connectors 32a, 32b to lead wires 34a, 34b, respectively.

A rod-shaped heater 36 for heating the sensor element 12 is provided in the sensor element 12. In fact, the heater 36 is inserted into and held in the sensor element 12 by means of a holder 38.

The heater 36 is electrically connected to an intermediate lead 30c, a connector 32c and a lead wire 32c.

In order not to cause conduction failure of the connectors 32a, 32b and 32c by electric contact thereof, they are, respectively, accommodated in separate through-holes formed in an insulator 40. In this way, the insulation between the connectors is ensured.

The lead wires 34a, 34b, 34c are passed through through-holes of a rubber bush 42 to outside of the air fuel ratio sensor.

In order that the rubber bush 42 not only acts to prevent infiltration of water and the like from the end face of the air fuel ratio sensor, but also fixes the lead wires 34a, 34b and 34c therewith, respectively, a cover 44 therefor is crimped from outside.

A method for fixedly holding the sensor element 12 in the accommodation hole 14a of the housing 14 is illustrated with reference to FIGS. 2a to 2c.

Figure 2A:
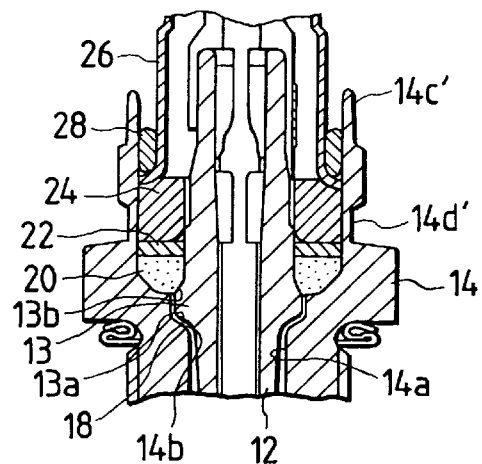
FIGS. 2a, 2b and 2c are, respectively, an illustrative view showing a method for making an air fuel ratio sensor of the invention.
Figure 2B:
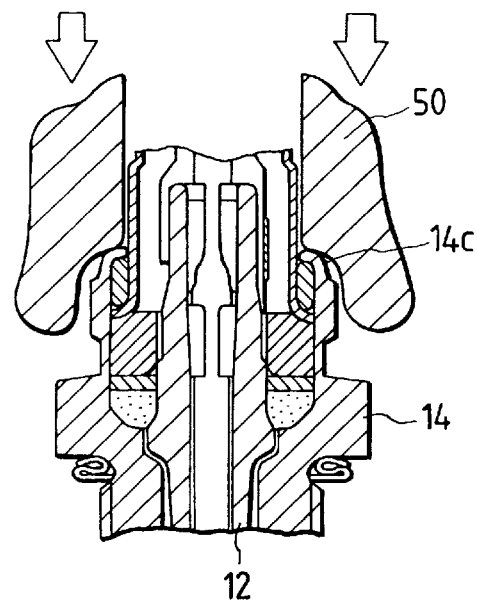

As shown in FIG. 2a, the sensor element 12 is inserted into the accommodation hole 14a of the housing until the lower end face 13a of the flange portion 13 of the element 12 is brought into contact with the tapered portion 14b of the housing 14 through the washer 18.

Thereafter, the insulating powder 20, the insulating ring 22 and the insulating ceramic member 24, the cover 26 and the ring 28 are placed on the upper face 13b of the flange portion 13 in this order as shown.

Subsequently, a cold crimping portion 14c' of the housing 14 is crimped by means of a jig 50 under a compression pressure, for example, of 3 tons. The resultant portion 14c is cold crimped as shown in FIG. 2b.

Figure 2C:
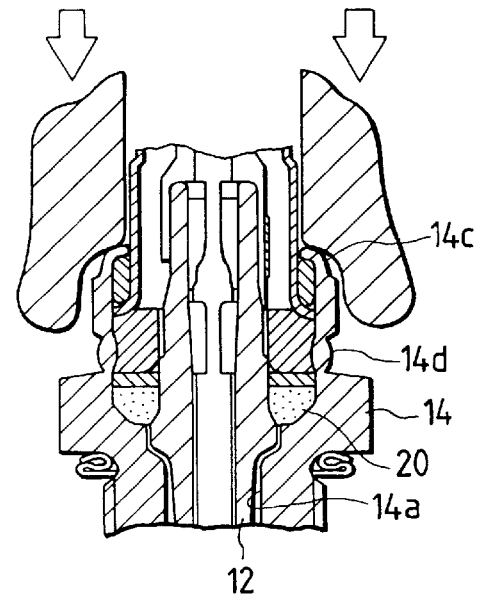

As shown in FIG. 2c, the compression pressure of the jig 50 which has compressed the cold crimping portion 14c' of the housing 14 is reduced to 1.5 tons, under which a current, for example, of 7.0 kA is passed to the housing for a time of 1 second or below to subject the housing to hot crimping. The hot crimping temperature should be lower than 1000° C., preferably 950° C. or below.

By the passage of the electric current, heat is concentrated on the thinnest portion of the housing, i.e. a hot crimping portion 14d', to deform the portion 14d' as shown in FIG. 2c. This deformation results in the deformation of the insulating powder 20 as shown thereby enhancing airtightness.

The hot crimping can thus realize reliable holding of the sensor element 12 within the accommodation hole 14a of the housing 14.

The thus obtained air fuel ratio sensor 10 exhibits not only good airtightness, but also a good corrosion resistance.

The influences of the amount of impurities in the housing 14 of the sensor 10 and the hot crimping temperature on a corrosion resistance are illustrated with reference to FIG. 3.

Figure 3:
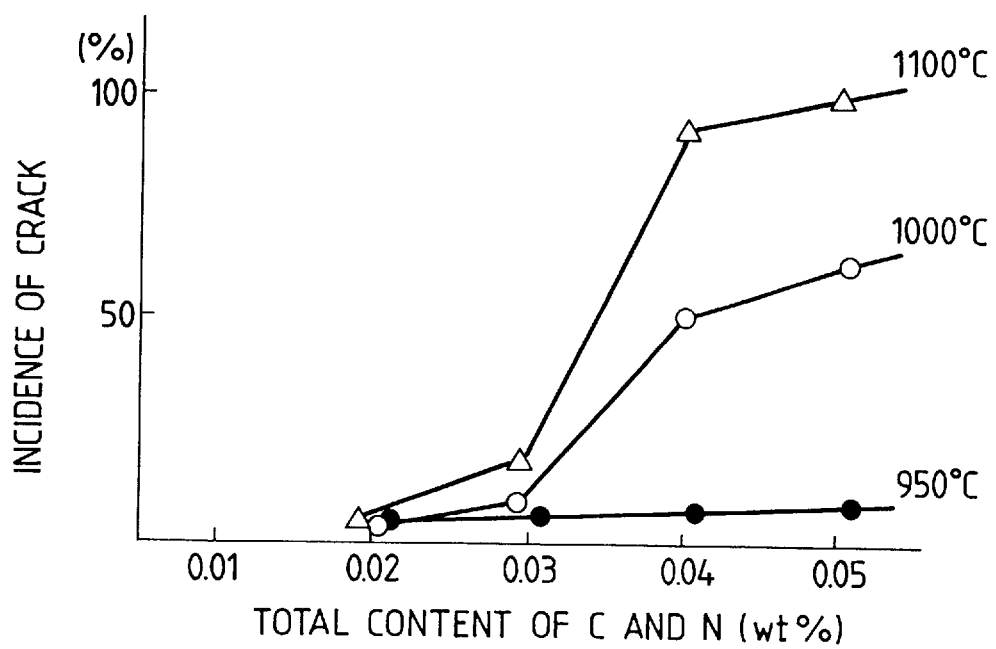
FIG. 3 is a graph showing a crack initiation rate in relation to the variation in content of C and N impurities in a housing for different average temperatures at the time of hot crimping.

FIG. 3 shows the relation between the incidence of crack and the total amount of carbon and nitrogen present in a ferritic stainless steel for the housing 14 for different average temperatures of 1100° C., 1000° and 950° C. at the hot crimping portion. It will be noted that the ferritic stainless steel used for this purpose consists primarily of SUS 403.

The incidence of crack was determined by subjecting 20 samples to hot crimping and then to microscopic inspection.

As will be apparent from FIG. 3, when the total amount of C+N was 0.03 wt % or below based on the stainless steel containing the C and N impurities, little crack was found in the samples at any tested average temperatures.

When the total amount of C+N was greater than 0.03 wt %, no crack was found when the average hot crimping temperature was lower than 1000° C. Preferably, the hot crimping temperature was found to be 950° C. or below, at which the incidence of crack was very low even when a total amount of the impurities reached 0.05 wt %.

As will be seen from the results of FIG. 3, when at least the portion 14d' of the housing which is to be hot crimped is controlled to have C and N impurities in a total amount of 0.03 wt % or below, little crack develops during the course of the hot crimping. The resultant housing becomes resistant to corrosion as a whole. In order to control the total amount of the C and N impurities only at the portion 14d', it is sufficient to treat the portion 14d' by de-carburization or de-nitriding known in the art. In order to avoid a complicated procedure of the local treatment for reducing the amount of the impurities, it is preferred that the housing is made entirely of such a ferritic stainless steel as defined before wherein the total content of N and C is 0.03 wt % or below.

Moreover, where the total amount of C+N is greater than 0.03 wt %, an average hot crimping temperature of lower than 1000° C., preferably 950° C. or below, is sufficient not to cause any crack in the hot crimped portion. Thus, the resultant housing exhibits a good corrosion resistance.

It is preferred in the practice of the invention that the thickness of the hot crimping portion 14d' of the housing 14 be uniform along the periphery thereof. Otherwise, heat would be concentrated only on a thinner portion, bringing about an average hot crimping temperature higher than as expected.

Figure 4:
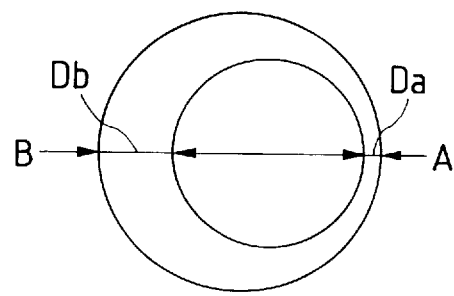
FIG. 4 is a schematic illustrative view illustrating the deviation in thickness of a thermally crimped portion of a housing.

FIG. 4 shows a schematic view illustrating a deviation in thickness of a hot crimping portion 14d' of the housing 14 where a minimum thickness portion is taken as Da and a maximum thickness portion is taken as Db as shown. A deviation relative to an average thickness is expressed according to the following equation $$\text{Deviation} = \frac{(Db - Da)}{(Da + Db)/2}$$

Figure 5:
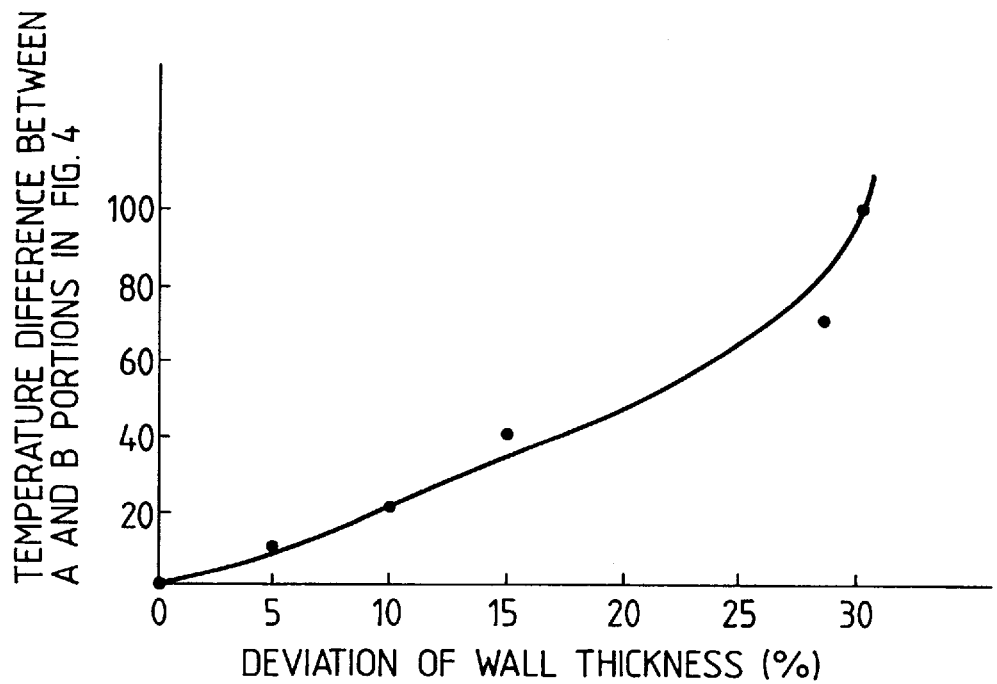
FIG. 5 is a graph showing the difference in temperature between two portions in relation to the variation in the deviation of a thickness at the crimped portion of a housing.

FIG. 5 shows a temperature difference between the A and B portions in FIG. 4 in relation to the variation in the deviation of thickness.

As will be apparent from FIG. 5, when the deviation is 15% or over, the temperature difference between the A and B portions exceeds 40° C. Thus, the temperature control at the hot crimping portion 14d' of the housing 14 becomes difficult. Thus, it is preferred that the deviation in thickness at the hot crimping portion of the housing should be within 15%.

What is claimed is:

1. An air fuel ratio sensor which comprises:

a sensor element having, at one side thereof, an elongated sensing portion closed at an end thereof and capable of detecting an air fuel ratio in a gas to be measured, a flange portion formed at an intermediate portion of said element, and a hollow portion extending from the flange portion at the other end of said element and having an open end; and a housing having an accommodation hole extending along an axial direction thereof and capable of accommodating said sensor element therein so that said sensing portion extends through the accommodation hole from one side of the housing, wherein the accommodation hole has a tapered inner wall serving as a stopper of said flange portion of said sensor element and said housing has a hot crimped portion at the other side thereof to fixedly hold the hollow portion of said sensor element within the accommodation hole, at least the hot crimped portion of said housing being made of a ferritic stainless steel with its composition comprising a content of carbon and nitrogen of 0.03 wt % or below.

2. An air fuel ratio sensor according to claim 1, wherein a deviation of a distance between an outer peripheral surface of said housing and an inner peripheral surface of said accommodation hole at a hot crimping portion prior to the hot crimping is less than 15% based on an average thickness of the hot crimping portion.

3. An air fuel ratio sensor according to claim 1, wherein said housing consists of a ferritic stainless steel product formed by cold forging.

4. An air fuel ratio sensor according to claim 3, wherein said housing is entirely made of a ferritic stainless steel which consists essentially of 16.0 to 18.0 wt % of Cr, 0.75 wt % or below of Si, 1.0 wt % or below of Mn, 0.04 wt % or below of P, 0.030 wt % or below of S, and a balance being Fe and inevitable impurities provided that a total amount of C and N is 0.03 wt % or below.

5. A method for making an air fuel ratio sensor of the type which comprises a sensor element having, at one side thereof, an elongated sensing portion closed at an end thereof and capable of detecting an air fuel ratio in a gas to be measured, a flange portion formed at the intermediate of said element, and a hollow portion extending from the flange portion at the other end of said element and having an open end, and a housing having an accommodation hole extending along an axial direction thereof and capable of accommodating said sensor element therein so that said sensing portion extends through the accommodation hole from one side of the housing, wherein the accommodation hole has a tapered inner wall serving as a stopper of said flange portion of said sensor element and said housing has a hot crimped portion at the other side thereof to fixedly hold the hollow portion of said sensor element within the accommodation hole, the method comprising forming said housing by cold forging, and hot crimping of the housing is performed under conditions of an average temperature lower than 1000° C. and one second or below.

6. A method according to claim 5, wherein a deviation of a distance between an outer peripheral surface of said housing and an inner peripheral surface of said accommodation hole at a hot spot portion which becomes the highest in temperature at the time of hot crimping is less than 15% relative to an average thickness of the hot spot portion.

7. A method according to claim 5, wherein the average temperature is 950° C. or below.

* * * * *